(12) United States Patent
Lombardi et al.

(10) Patent No.: US 6,779,937 B1
(45) Date of Patent: Aug. 24, 2004

(54) ACCESSORY GRIP FOR ELONGATE INSTRUMENT

(75) Inventors: Carl Lombardi, Lloyd Harbor, NY (US); Morris Sussman, Bellmore, NY (US)

(73) Assignee: Lombardi Design & Manufacturing, Freeport, NY (US)

( * ) Notice: Subject to any disclaimer, the term of this patent is extended or adjusted under 35 U.S.C. 154(b) by 0 days.

(21) Appl. No.: 10/677,971

(22) Filed: Oct. 2, 2003

(51) Int. Cl.[7] .................................................. A46B 5/02
(52) U.S. Cl. ............................................................ 401/6
(58) Field of Search ................................ 401/6, 48, 88; 15/443, 435, 247; 16/430, 421; 264/271.1, 267, 173.16, 176.1, 322, 222; 81/489

(56) References Cited

U.S. PATENT DOCUMENTS

| | | | | |
|---|---|---|---|---|
| 768,935 A | * | 8/1904 | Goldsmith | 49/209 |
| 770,363 A | * | 9/1904 | Goldsmith | 15/443 |
| 779,082 A | * | 1/1905 | Huber | 15/443 |
| 782,388 A | * | 2/1905 | Goldsmith | 15/443 |
| 1,706,326 A | * | 3/1929 | Shaukis | 15/444 |
| 2,594,955 A | * | 4/1952 | Markowitz | 248/683 |
| 4,056,325 A | * | 11/1977 | Maruyama | 401/65 |
| 6,186,685 B1 | * | 2/2001 | Salemme | 401/6 |
| 6,273,626 B1 | * | 8/2001 | Yazawa | 401/6 |
| 6,447,190 B1 | * | 9/2002 | Kwitek | 401/6 |

* cited by examiner

Primary Examiner—Gregory L. Hudson
Assistant Examiner—Huyen Le
(74) Attorney, Agent, or Firm—Bradley N. Ruben

(57) ABSTRACT

A grip accessory, especially for a writing instrument such as for a convention pencil or pen, a cosmetics pencil or applicator, a medical instrument, or the like. The device has a core with a bore made from a material that slides relatively easily over the instrument, an aperture in the core, and an elastomeric sheath with protrusions that extend through the aperture and into the bore. The protrusions provide resistance to the sliding fo the instrument through the bore when the instrument's outer surface engages the protrusions, thereby keeping the grip accessory in place but allowing the accessory to be place on and removed from the elongate instrument.

13 Claims, 1 Drawing Sheet

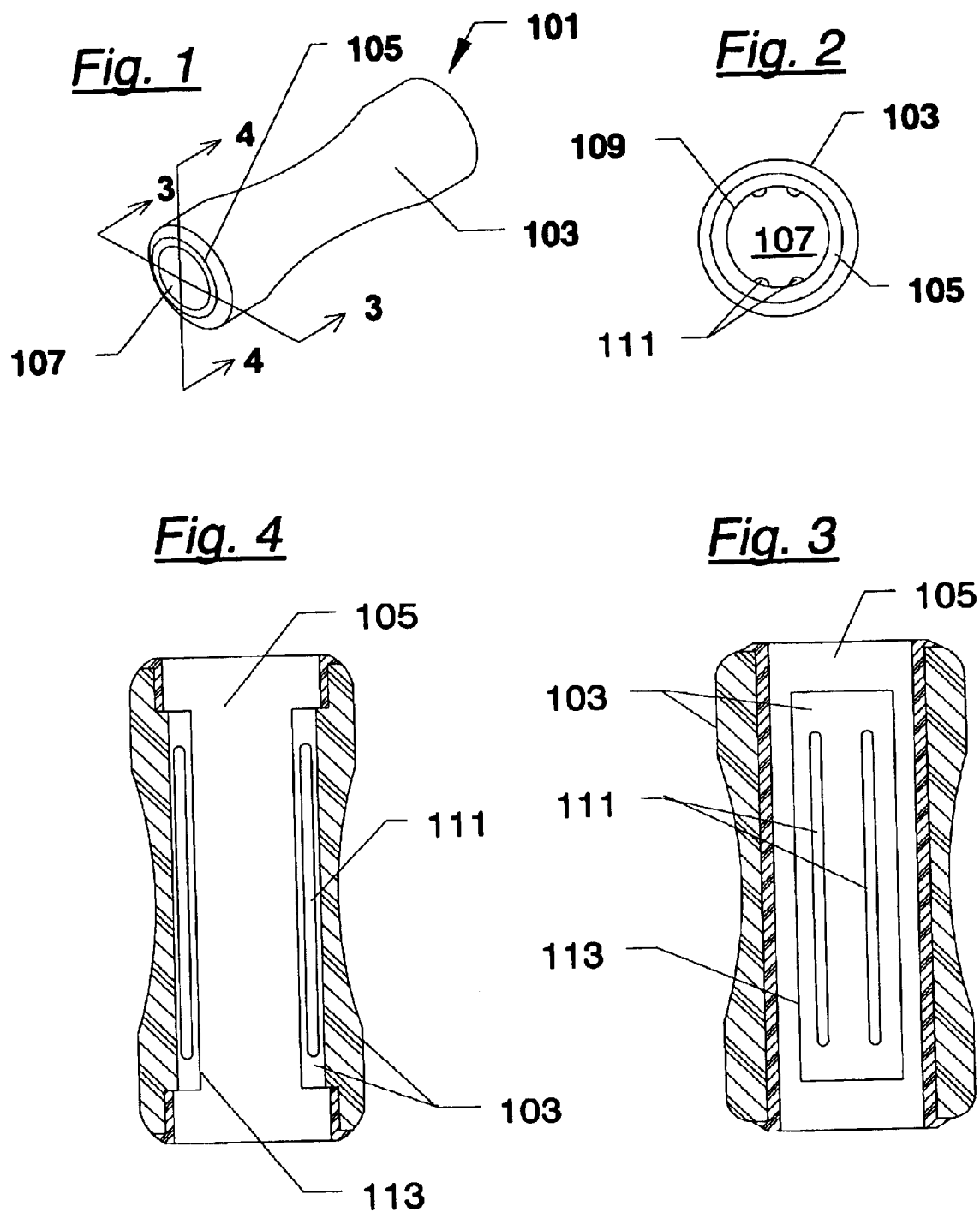

US 6,779,937 B1

ACCESSORY GRIP FOR ELONGATE INSTRUMENT

BACKGROUND OF THE INVENTION

1. Field of the Invention

This invention relates to an accessory grip for use with an elongate instument, such as a writing pencil or a cosmetics pencil, and to a method for making the same.

2. The State of the Art

Since the vulcanization of rubber, various natural and synthetic polymers have been formed into aids for gripping objects. A common grip aid prevalent now is on writing pens, where the elonate pen's plastic body is molded with, or overmolded with, a soft polymeric grip, such as described in U.S. Pat. No. 6,036,385. Another common grip aid is one which is made separately and the user then places over a pen or pencil. Such devices are described in the following U.S. Pat. Nos. 4,601,598; 4,689,020; 4,832,604; 4,932,800; 5,056,945; 5,143,463; 5,876,134; 6,019,534; 6,347,898; and 6,439,791. Various designs for these slip over grip accessories are also prevalent, such as U.S. Des. Pat. No. 414,807. (The disclosures of all of the foregoing patents are expressly incorporated herein by reference.)

Problems with slip over grip accessories for writing implements are due to such devices being made of a single, unitary material that must accommodate multiple, often contradictory functions, such as easy sliding placement over the implement, and staying in position and not sliding off once placed.

SUMMARY OF THE INVENTION

In light of the foregoing, various objects of this invention are to provide an improved grip accessory that is easier to slide onto an elongate instrument, while maintaining the placement of the accessory after placement.

In one embodiment the inventive grip accessory comprises an inner portion or core comprising a relatively non-elastomeric material surrounded by outer portion or sheath having a relatively elastomeric material, the entire accessory having a bore adapted to accept an elongate instrument. In related embodiments, the core has at least one aperture and the outer portion has at least one ridge that extends through the aperture to engage the outer surface of an elongate instrument inserted into the bore.

In another embodiment this invention provides a method for manufacturing a grip accessory having an outer portion and an inner portion, comprising injection molding said inner portion from a non-elastomeric polymeric composition and overmolding onto said inner portion an outer portion from an elastomeric polymeric composition.

BRIEF DESCRIPTION OF THE DRAWINGS

FIG. 1 is a perspective view of a grip accessory.

FIG. 2 is an end view of a grip accessory.

FIG. 3 is a cross section taken along line 3—3 shown in FIG. 1

FIG. 4 is a cross section taken along line 4—4 shown in FIG. 1.

DETAILED DESCRIPTION OF SPECIFIC EMBODIMENTS

The use of grip accessories for elongate instruments like pens, pencils, and the like is well-known. Such grip accessories that are not molded directly and permanently onto the instrument are uniformly made of an elastomeric material that is slid over the instrument.

FIG. 1 is a perspective view of the grip accessory 101 having sheath 103 and an core 105 defining an inner surface of the bore 107 extending the length of the accessory.

FIG. 2 is an end view along the bore showing the inner and outer portions, the inner surface 109 of the core defining the bore, and a plurality of ridges 111 extending past the inner surface into the bore.

FIG. 3, a cross section taken along line 3—3 in FIG. 1, shows the bore extending the length of the device. The core and sheath also extend essentially the entire length of the bore. The sheath is shown with a slightly convex surface to provide an ergonomic aspect, and can be provided with ridges, stippling, or the like to provide a desired aesthetic or feel to the device to the outer surface of the device. The core has an aperture 113 extending partially along the bore so that a portion of the sheath is exposed to the bore. The inner exposed portion of the sheath is provided with ridges 111 that extend past the inner surface 109 of the core into the bore 107. Instead of or in addition to one or more ridges, the sheath can provide any type of protrusion that extends through the aperture into the bore.

FIG. 4 is a cross section taken along line 4—4 of FIG. 1 which is 90° to line 3—3. As shown, the core has two aperatures and the sheath provides two pair of ridges.

The device is sized so that when it is placed over an elongate instrument, the ridges engage the outer surface of the instrument. Although shown with a round bore, it should be apparent that the bore can be of any geometry to accommodate the outer geometry of any elongate instrument. Further, the bore can be conical to accommodate an instrument having a girth that increases from the end of the instrument.

The core is preferably made of a material that is rather inelastic and has a hard, smooth surface. Preferred materials include polyalkylenes such as polyethylene, polypropylene, and polybutylene. Other polymeric compositions, such as poly(vinyl chloride), nylon, or polyacrylate can also be suitable. In addition, the core may be made of metal, ceramic, or wood, although polymers are preferred. The polymer used for the core can be plasticized so that it is flexible, but should be inelastic with respect to the sheath so that it slides relatively easily over the surface of the elongate instrument for which the grip accessory is desired.

The sheath is preferably made from an elastomeric material, such as polyisobutylene, a polyurea, or the like. Suitable elastomeric polymers are well-known and often used in the prior art slidable grip accessories; and commercially available (e.g., Versaflex brand polyurea elastomers from VersaFlex, Inc., Kansas City, Mo., and Santoprene brand thermoplastic elastomers from Advanced Elastomer Systems, Akron, Ohio). The material for the sheath can be chosen with a desired hardness, moisture resistance, or other property as desired. Hypoallergenic polymers are also suitable. The sheath material should provide a comfortable feel to the user, and provide some resistance to the sliding of the elongate instrument through the bore when the instrument engages the ridges. Accordingly, the sheath can be tacky instead of, or in addition to, being elastomeric, as either property provides resistance to a surface sliding thereover.

The grip accessory as described herein is preferably made by injection molding, such as bi-injection molding or overmolding. For example, a mold having two ports is used; the core is molded from a desired polymer using one of the ports, and then the sheath material is introduced through the other port and is molded over the core. The core and sheath materials are preferably chosen so that they are compatible and melt bond during the molding process, or have sufficient compatibility so that they do not delaminate from each other.

The grip accessory is preferably used in combination with a writing pen or pencil, or a cosmetics pencil or applicator. The grip accessory can also be used with a medical instrument, such as a retractor, or a dental instrument such as a curette or scaler.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A grip accessory, comprising: a core both defining a bore adapted to removably receive an elongate instrument slid thereinto and comprising a relatively non-elastic material having a surface and an integral sheath formed over the core for providing a comfortable gripping surface and also engaging a portion of the surface of an elongate instrument in the bore.

2. The grip accessory of claim 1, wherein the core includes at least one aperture, and the sheath includes at least one protrusion that extends through the aperture into the bore effective to contact said elongate instrument placed in the bore.

3. The grip accessory of claim 2, wherein the protrusion is a ridge.

4. The grip accessory of claim 3, wherein the core is comprised of polyethylene, polypropylene, or polybutylene.

5. The grip accessory of claim 4, wherein the sheath is an elastomer.

6. The grip accessory of claim 3, wherein the sheath is an elastomer.

7. The grip accessory of claim 2, wherein the core is comprised of polyethylene, polypropylene, or polybutylene.

8. The grip accessory of claim 7, wherein the sheath is an elastomer.

9. The grip accessory of claim 2, wherein the sheath is an elastomer.

10. The grip accessory of claim 1, wherein the core is comprised of polyethylene, polypropylene, or polybutylene.

11. The grip accessory of claim 10, wherein the sheath is an elastomer.

12. The grip accessory of claim 1, wherein the sheath is an elastomer.

13. A method for making a grip accessory, comprising:

A. molding from a first material a core having a bore and at least one aperture; and B. molding over the core a sheath of a second, elastomeric material, having a geometry that includes at least one protrusion that extends past the aperture into the bore, wherein the first material and the second material bond during the molding process.

* * * * *